United States Patent [19]
Tuneberg

[11] Patent Number: 5,441,409
[45] Date of Patent: Aug. 15, 1995

[54] ORTHODONTIC BAND

[75] Inventor: Lee H. Tuneberg, Sheboygan, Wis.

[73] Assignee: American Orthodontics Corporation, Sheboygan, Wis.

[21] Appl. No.: 200,371

[22] Filed: Feb. 23, 1994

Related U.S. Application Data

[63] Continuation of Ser. No. 10,416, Jan. 28, 1993, abandoned.

[51] Int. Cl.⁶ .................................................. A61C 3/00
[52] U.S. Cl. ........................................ 433/23; 428/687
[58] Field of Search ................. 433/23, 9; 428/577, 428/601, 687

[56] References Cited

U.S. PATENT DOCUMENTS

| | | | |
|---|---|---|---|
| 4,243,386 | 1/1981 | Kawaguchi | 433/9 |
| 4,369,033 | 1/1983 | Webb et al. | 433/9 |
| 4,661,059 | 4/1987 | Kanno | 433/9 |
| 4,752,221 | 6/1988 | Hanson et al. | 433/9 |
| 4,840,562 | 6/1989 | Wilson et al. | 433/23 |
| 4,842,513 | 6/1989 | Haarmann | 433/9 |

OTHER PUBLICATIONS

American Orthodontics Catalog, 1985, pp. 1 and 23.
Seeholzer, Dr. Hans W., and Dr. Walter Dasch, "Banding with a Glass Ionomer Cement, Journal of Clinical Orthodontics", vol. XXII, No. 3, 1988, pp. 165–169.

Primary Examiner—Cary E. O'Connor
Attorney, Agent, or Firm—Lloyd L. Zickert

[57] ABSTRACT

An orthodontic band having a textured inner surface for enhancing the adhesive bonding to a tooth, wherein the textured surface is formed by photoetching a pattern of pockets, indentations, or raised portions.

27 Claims, 1 Drawing Sheet

ORTHODONTIC BAND

This application is a continuation of application Ser. No. 08/010,416, filed Jan. 28, 1993, abandoned.

This invention relates in general to an orthodontic band, and more particularly to an orthodontic band having a textured inner surface for enhancing the strength of cement bonding the band to a tooth, and still more particularly to an orthodontic band having a textured inner surface where the textured surface is formed by photoetching a pattern of pockets, recesses, or raised dots on the surface.

BACKGROUND OF THE INVENTION

Orthodontic bands serve an important function during the orthodontic treating of a patient to correct malocclusions. Such bands may be applied to all of the teeth or only to anchor teeth in accordance with the particular technique preferred by the orthodontist. Importantly, the bands reduce tendencies for carious attack on the tooth due to their circumferential protection of the enamel. Additionally, they are important in that they allow secure attachment of various brackets or tubes to the teeth that facilitate orthodontic biomechanics. Finally, the bands serve to more evenly distribute a tooth-moving force over the area of an individual tooth.

The use of orthodontic bands has always been common to the profession of orthodontics either through manual "pinching" of bands or the more modern seamless ring-shaped bands. Another historic problem has been associated with their benefits in that the cement or adhesive seal between the inner band surface and the luting medium tends to loosen and allow dislodging of the band. Loose bands may occur from many different situations such as because of occlusal forces, extraoral tractive forces, masticatory forces from food bolus, or even improper sizing and seating. Additionally, luting agents may be mixed improperly or moisture may be introduced into the agents prior to complete cement setup.

Clinically, loosened bands can lead to micro-leakage of electrolytes or other contaminants which often cannot be detected through the normal course of orthodontic treatment. Upon removal of a loose band at the end of treatment, it may then be discovered that deleterious effects of cement seal failure have caused decalcification or carious attack of the tooth surface. Other clinical problems resulting from loose bands include the frustration of emergency office visits and the scheduling of extra appointments to clean the tooth and re-cement another band for the continuance of orthodontic treatment. Additionally, there may be a relapse of desired tooth movement prior to the replacement of a loose or dislodged band.

Heretofore, it has been known to apply metal mesh to at least parts of the inner surfaces of bands to increase tension. While some increased tension is obtained, the mesh takes up room by increasing the thickness of the band at the area of mesh attachment. Further, an extra step in manufacturing of the band is required in applying the mesh after the band has been completely formed. That the mesh takes up room affects the fit of the band on the tooth in an adverse manner.

It has also been proposed to sandblast the inner surface of bands to increase the luting agent strength between the band and the cement. This method of texturizing the inner surface is undesirable because it becomes a costly secondary operation following band manufacture.

It has also been proposed to acid-etch the band material prior to formation of the band so that the retention can be increased. This method produces a minimal texture and can be lost in further manufacturing steps because of close tool/material tolerances. Further, increased tool wear and replacement costs become burdensome.

Machined or engraved physical grooves could be employed on the stainless steel foil prior to band manufacture. Because foil thickness is usually 0.005 to 0.007 inch, and therefore generally about 0.006 inch thick, depth tolerance problems become critical and tear or tensile weakness in the foil becomes a problem when the band is completed.

It has also been known to photoetch blind holes into the base member of an orthodontic bracket which is thereafter sandblasted for roughening purposes to give the best holding strength, as disclosed in U.S. Pat. No. 4,243,386. It has also been known to texture the tooth-attaching sides of brackets in other ways in order to increase retention with a bonding adhesive.

SUMMARY OF THE INVENTION

The orthodontic band of the present invention provides a textured inner surface for enhancing cement bonding on a tooth by photoetching a pattern on the band material prior to making of the band. The photoetch pattern does not take up room as does the addition of mesh and the etch process can be closely controlled to define pockets, indentations, or raised dots that do not affect the integrity of the band material and which provide a uniform surface for enhancing the cement bonding.

The texturing of the cement surface of the band according to the present invention is formed by photoetching prior to the formation of the band and during the die working of the band to form a ring-shaped body that is then finally contoured for a particular tooth. The photoetch pattern may take the form of a multiplicity of pockets in rows that are placed so that pockets in adjacent rows are aligned or staggered. Alternately, the pattern may take the form of doughnut or polygonally shaped recesses. Likewise, the pockets may be round or polygonally shaped, and it should be appreciated that on any one surface a combination of various shaped pockets and/or various shaped recesses may be part of the pattern for defining the textured surface.

It is therefore an object of the present invention to provide a band material having a photoetched surface on one side that becomes the inner surface of a finely formed band for enhancing the cement bonding of the band onto a tooth.

It is a further object of the present invention to provide an orthodontic band with an inner textured surface capable of withstanding increased forces from occlusal or masticatory movements, thereby increasing dislodgment pressure by providing a textured surface which more tenaciously allows the luting medium to adhere.

It is a further object of the invention to texture the inner surface of band material prior to the actual manufacture of the band such that substantial labor savings are realized because the texturing of the surface does not become a secondary operation on a finished product.

It is a still further object of the present invention to provide an improved orthodontic band having an inner textured surface by providing a photoetched pattern on that surface prior to band formation whereby through the stretching and deforming of the ring blank into the anatomical shape of a tooth the photoetched pattern yields true mechanical undercuts randomly arranged on the band surface.

Another object of the present invention is in providing an improved orthodontic band that materially enhances cement bonding to a tooth where photoetching a pattern onto the band material prior to band formation enhances high-production capabilities and whereby the textured surface produced increases luting agent adherence to the band substrate, resulting in better retention of bands on teeth during orthodontic treatment.

Other objects, features and advantages of the invention will be apparent from the following detailed disclosure, taken in conjunction with the accompanying sheets of drawings, wherein like reference numerals refer to like parts.

DESCRIPTION OF THE INVENTION

Figure 1:
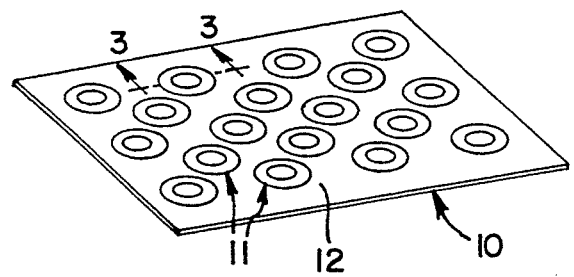
FIG. 1 is a perspective view of banding material in sheet form that has been photoetched with a pattern on one side and illustrating the photoetched side.
Figure 2:
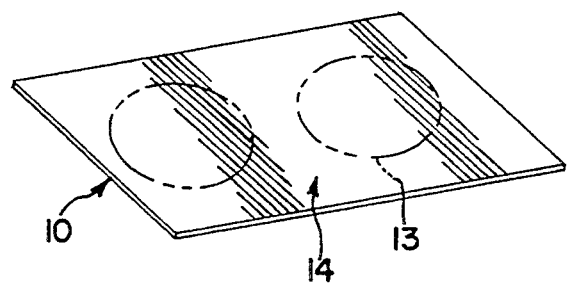
FIG. 2 is a perspective view of the sheet of material in FIG. 1 and showing the opposite side.
Figure 3:
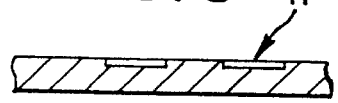
FIG. 3 is an enlarged sectional view taken along line 3—3 of FIG. 1.

Referring now to the drawings, and particularly to FIGS. 1 to 5, the metal banding material to form the orthodontic bands according to the invention is in sheet form initially, as indicated by the numeral 10 in FIGS. 1 and 2, and having a photoetched pattern 11 on side 12 and a smooth surface on the opposite side 13. This band material thickness is from 0.005 to 0.007 inch and therefore about 0.006 inch in thickness and would have a width sufficient so that circular ring blanks could be stamped from the material that later could be die-worked to form a ring blank, as shown by the ring blank 10A in FIG. 4. The ring blank is formed by subjecting the band blank as illustrated by the dotted configuration 14 in FIG. 2 through a series of punch dies having close tolerances where the band blank would be worked into a hat-shaped form and then have the end wall cut off to form the ring blank 10A. Thereafter, the ring blank 10A would be subjected to additional die-forming steps to form an anatomically shaped bracket for fitting to a tooth, such as illustrated by 10B in FIG. 5. During die working to form the ring blank and the anatomical shape, the etched patterns will be distorted, thereby changing its form and geometry such as to produce some true undercuts that will enhance luting strength.

While the above formation of an orthodontic band will provide a seamless band of the type preferred today in orthodontics, it can be appreciated that the band material which may be in the form of a roll of material could be provided for custom formation of bands by applying a section of material about a tooth and pinching the ends together so that they could be provided in overlapped form for welding to ultimately custom make a band for a tooth.

With respect to the photoetched pattern 11 on the band material 10, the pattern is in the form of a plurality of doughnut-shaped recesses arranged in rows where adjacent rows are staggered. The size of the outside diameter may be whatever is desired. For example, relative to one specimen of a band with this photoetched pattern as will be set forth below, the outer diameter is 0.040 inch with an inner island of 0.030 inch, leaving an annular recess with a width of 0.010 inch and also having an etched depth of about 0.001 inch. The doughnut-shaped recesses are spaced apart center-to-center approximately 0.120 inch with spacing of 0.060 inch between centers at a 45 degree diagonal.

Other forms of recesses with islands are shown in FIGS. 6 to 9 wherein a photoetched pattern having a square recess is shown in the band material 20. A photoetched pattern having triangular recesses is shown in the band material 21. A photoetched pattern having rhomboidal recesses is shown in the band material 22 and a photoetched pattern having hexagonal recesses is shown in the material 23 of FIG. 9. It will be appreciated that any suitable polygonal shape may be employed as well as any round or oval type shape of recess. Further, it should be appreciated that any combination of sizes and shapes of recesses may be employed in a photoetched pattern.

Figure 11:
FIG. 11 is an enlarged sectional view taken along line 11—11 of FIG. 10.
Figure 10:
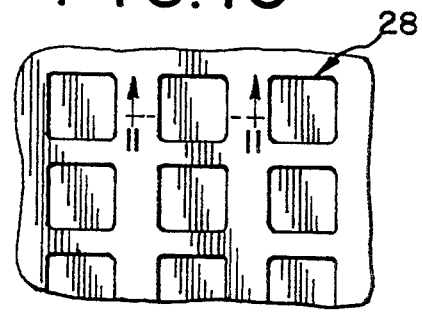
FIG. 10 is a view of a still further modified photoetched pattern on band material wherein the pattern is in the form of square pockets.
Figure 4:
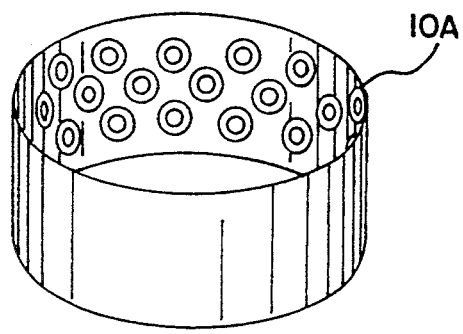
FIG. 4 is a perspective view of a ring-shaped blank for an orthodontic band having the photoetched pattern of FIG. 1 which has been accomplished by a series of die-working steps.
Figure 5:
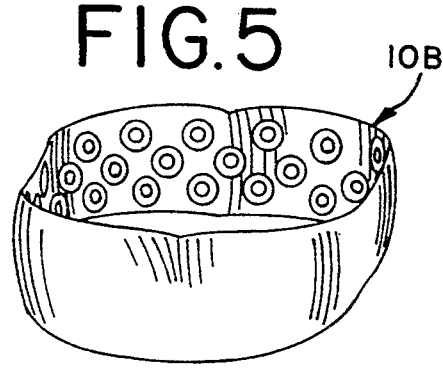
FIG. 5 is a perspective view of an anatomically shaped orthodontic band formed from the ring blank of FIG. 4.
Figure 6:
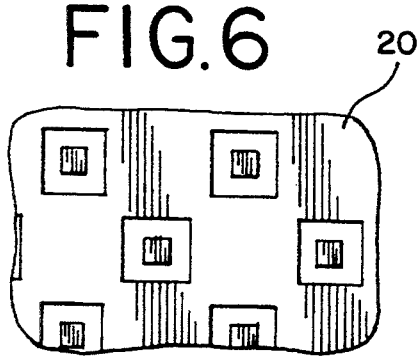
FIG. 6 is a fragmentary plan view of band material showing a modified pattern of square shaped recesses as an alternative to the doughnut shaped recesses in the embodiment of FIGS. 1 to 5.
Figure 7:
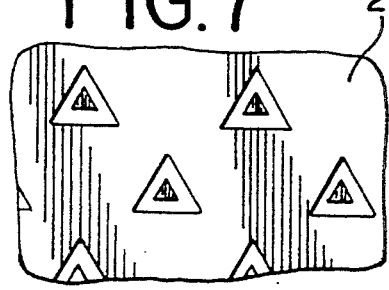
FIG. 7 is a fragmentary enlarged plan view of a further modified photoetched pattern where the pattern is in the form of triangular recesses.
Figure 8:
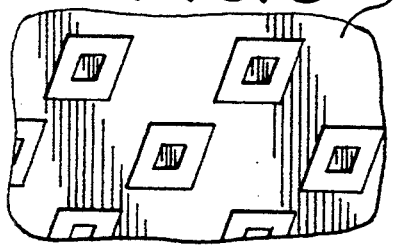
FIG. 8 is a further modified photoetched pattern where the pattern is in the form of rhomboidal recesses.
Figure 9:
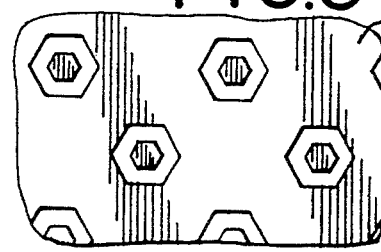
FIG. 9 is a view like FIG. 6 showing a still further modified photoetched pattern in the form of hexagonal recesses.

Another form of photoetched pattern is shown in FIGS. 10 and 11 wherein the photoetched pattern includes a plurality of rows of square-shaped pockets 28 wherein the pockets are arranged in rows with pockets of adjacent rows aligned with one another. It should be appreciated that the pockets in adjacent rows could be staggered with respect to each other if desired. Moreover, it should be appreciated that the shape of the pockets may be round or polygonal where the same shape is used on one photoetched pattern or multiple shapes are used in a photoetched pattern. It should further be appreciated that for purposes of clarity the photoetched patterns illustrated in the embodiments in the drawings are in exaggerated size as the dimensions and spacings of the pockets or recesses would be such as to provide the best possible retention.

A suitable band material would be 0.006 inch thick 300 series stainless steel, but it should be appreciated that other thicknesses and types of stainless steel could be employed.

The photoetching process of the stainless steel band material includes cleaning the surface to be photoetched with a hot alkaline soak followed by a water rinse and a light pickle to activate the surface. An aqueous film photoresist is laminated to the prepared surface and the material is then placed in a glass or film photo tool where it is exposed to a UV light source for a period of time dictated by the type of photoresist used. Following exposure of the photoresist to the pattern, a hold time of about fifteen minutes is maintained prior to developing away unexposed photoresist. Development is accomplished by spraying a development solution such as sodium carbonate onto the photoresist followed by an air dry operation and a post-bake operation which cross-links the photoresist on the stainless steel material. Etching of the stainless steel is then accomplished by using a standard etchant such as a ferric chloride. The etching process is adjusted for the desired etch rate in depth by modifying etchant Baumé or temperature and speed.

Following etching, the stainless steel material is then rinsed with water and dried. Excess photoresist is then stripped from the stainless steel material by employing spray solutions such as ethanolamine-based chemistry. Following stripping of photoresist, the stainless steel material is dried with hot air and ready for processing into orthodontic ring blanks or bands.

In order to test the luted tensile strength of textured surfaces of stainless steel material, seven samples of stainless steel band material with varying textured surfaces and one sample of untextured material used as a control were evaluated by cutting strip specimens from each of the seven textured stainless steel foils and the control. Because the material thickness of each was 0.006 inch and very thin, the non-treated surfaces were glued to a supportive backplate to provide rigidity. They were glued by using a cyanoacrylate adhesive. The specimens were approximately 0.400 inch wide and one inch in length. The textured surfaces were lap bonded together using a glass ionomer cement with an overlap area of approximately 0.400 inch by 0.400 inch. The chosen cement was Ketac-Cem distributed by ESPE-Premier Sales Corp. of Norristown, Pa. Ketac-Cem is a trademark owned by ESPE, and this cement was selected because it is supplied in a premeasured capsule reducing chances for error in mixing and increasing comparison test uniformity. These prepared bonded samples were then stored in 100 percent humidity at a temperature of 37 degrees C. for a period of 24 hours.

Tensile pulls were performed on the samples using an Instron Model 1000 testing machine with a crosshead speed of 0.5 inch per minute, and a 100 pound load cell set at the fifty-pound range. The load cell for one of the samples was set at the 100 percent range. The textured surfaces of the samples were as follows:

1) Sandblast: Specimens were blasted with 0.009 inch (avg) glass beads with air pressure of 110 PSI for 20 seconds. This produced a textured surface on one side of the material with an Ra of 0.48 (avg).

2) Emery cloth: Specimens were abraded on one surface using emery cloth of 120 grit/texture. Surface texture after abrasion measured 0.34 Ra (avg).

3) Bead blast: Specimens were textured using 50 um tungsten carbide course beads at 100 PSI air pressure for 20 seconds. This produced a surface finish on one side of the stainless sheet of 0.68 Ra (avg).

4) Wire wheel: Specimens were textured on one surface by feeding the stainless strip under a constant pressure through a tempered carbon steel abrasive wire wheel. Wire bristles were approximately 0.010 inch in diameter by 0.400 inch in length, with a wheel speed of 1700 RPM. This produced a surface finish of 0.10 Ra (avg).

5) Photoetch—small uniform pockets: Specimens were photoetched (Buckbee-Mears Corporation of St. Paul, Minn.) by above description to a geometry of recessed "pockets" measuring approximately 0.0035 inch × 0.0035 inch with spacing of approximately 0.005 inch and a depth of approximately 0.001 inch like illustrated in FIGS. 10 and 11.

6) Photoetch—micro-raised dots: Specimens were photoetched pursuant to the previous process with the resultant stainless steel specimen exhibiting a surface characterized by small raised dots (surrounding surface etched away) approximately 0.003 inch in diameter by 0.001 inch in height and separated by a distance of approximately 0.006 inch.

7) Photoetch—recessed doughnuts: Specimens were photoetched as before to a geometry characterized by uniform annular recess approximately 0.040 inch in outside diameter with 0.010 inch etched wall thickness defining a 0.030 inch diameter island and an etched depth of approximately 0.001 inch. Etched doughnuts were approximately 0.120 inch apart center-to-center with 0.060 inch spacing between centers at a 45° diagonal like generally illustrated in FIG. 1.

8) Control: Standard stainless strip material such as used with American Orthodontics 8800/8900 Series molar bands was used as the control. Surface finish on the pre-die material was 0.00 Ra.

Following preparation of the surfaces and prior to testing, all samples were ultrasonically cleaned in acetone followed by Freon TF and a methanol rinse.

Bond stress at break was then converted to $KG/CM^2$ with the following results:

| Sample | Break | Load Cell Range |
| --- | --- | --- |
| Sandblast | 5.8 | 50 |
| Emery cloth | 8.9 | 50 |
| Bead blast | 6.5 | 50 |
| Wire wheel | 4.1 | 50 |
| Photoetch (small pockets) | 16.5 | 50 |
| Photoetch (raised dots) | 22.9 | 100 |
| Photoetch (recessed doughnuts) | 7.6 | 50 |
| Control | 3.9 | 50 |

As previously indicated, the prepared sample strips of band foil were in flat cross section. The above tests and resulting data show that surface treatment of band material can lead to increased cement strength loads which decreases probability of loose bands during orthodontic treatment. However, orthodontic bands are generally manufactured as seamless ring blanks and stretched into a mirror of tooth anatomy or are produced as finished seamless anatomical bands. Both ring blanks and anatomical bands may be made on a progressive die machine or the equivalent. As flat stainless steel strip stock is fitted into a press and a circular blank is stamped, close tolerance punches/dies gradually draw and form the stainless steel material into a ring with or without anatomical detail. Due to very tight tolerances between punch/die and the material thickness, any raised surfaces on the interior side of the stainless foil will have a tendency to be smooth or reduced in surface texture. Because of this well known phenomena, samples of photoetched stainless steel band material were further subjected to the manufacture of ring blanks to determine the effect of surface texturing. Materials with surfaces treated by emery cloth, wire wheel, sandblasting, or bead blasting would expect to have substantially the same strength as untreated materials.

The testing included the mounting of bovine teeth in acrylic tubes. The teeth were prepared for banding using conventional methods of scaling and pumicing. Ring blanks from the above textured stainless steel foils and the control were cut occlusogingivally at the buccal high point and adapted to the bovine crown. While the ends of the slit ring blank were pinched with a hand plier, the stainless steel foil was burnished to conform to the tooth anatomy. With the plier still gripping the foil, the band was removed and spot-welded at the juncture point. Thereafter, two stainless steel buttons of the type sold by American Orthodontics Corporation of Sheboygan, Wis., under Model number 852-170 were welded to the band, one on the facial side and one on the lingual side. These buttons provide an anchor for allowing the application of force to break the cement seal between a band and a tooth. The bands were then cemented to the teeth using the above identified glass ionomer cement. It is well known that such a cement chemically bonds to the tooth enamel, while only very weakly bonding to stainless steel. Thus, it is recognized that clinical loosening of bands on teeth fail at the cement/stainless steel band interface.

The acrylic tubes were mounted in the lower jaw of an Instron Model 1000 testing machine. Two 0.020 inch diameter spring temper stainless steel wires were fixtured in the upper jaw. The wires were adapted to fit into the undercuts of the buttons. The bands were then pulled from the teeth with a crosshead speed of 0.5 inch per minute with a 100 pound load cell set in the 100 pound range. The following test results were recorded:

| Sample | Shear Pounds to Dislodge Band from Tooth | % Increased Retention over Control |
|---|---|---|
| Photoetch (small pockets) | 77.9 | 66% |
| Photoetch (raised dots) | 55.4 | 18% |
| Photoetch (recessed doughnuts) | 63.8 | 30% |
| Control | 46.9 | |

Further, an analysis was made of the inside surface of the bands following dislodging from the teeth to determine subjectively the percent of cement remaining on the inside surface of the dislodged bands. This provides an indication of the plane of failure along the cement and shows that the control sample failed closest to the interface of the band and adhesive. The following results were recorded:

| Sample | % Cement Remaining on Inside Surface of Dislodged Band |
|---|---|
| Photoetch (small pockets) | 44.4% |
| Photoetch (raised dots) | 55.5% |
| Photoetch (recessed doughnuts) | 25.6% |
| Control | 21.0% |

In view of the foregoing, it is appreciated that the photoetched texturing of the inside band surfaces materially increases the retention of the bands on the teeth, thereby materially increasing the efficiency of orthodontic treatment.

It will be understood that modifications and variations may be effected without departing from the scope of the novel concepts of the present invention, but it is understood that this application is to be limited only by the scope of the appended claims.

The invention is hereby claimed as follows:

1. Metal band material adapted to be cut into circular blanks and die-worked for making tubular orthodontic bands, said material being in flat sheet or strip form of a thickness such that it will function as an orthodontic band when die-worked into a tubular band and being photoetched on one side which becomes the inside surface of the band and the side to be engaged by dies during die-working into tubular bands, and said photoetched side including a plurality of spaced apart indentations each having a centrally disposed island, whereby said indentations coact with cement when attaching the band to a tooth with a dental cement to materially enhance the strength of the cement bond between the band and the tooth.

2. The band material of claim 1, wherein the indentations are arranged in rows with the indentations in adjacent rows being aligned.

3. The band material of claim 1, wherein the indentations are arranged in rows with the indentations in adjacent rows being staggered.

4. The band material of claims 2 or 3, wherein the indentations are doughnut-shaped.

5. The band material of claims 2 or 3, wherein the indentations are polygonally shaped.

6. The band material of claims 2 or 3, wherein the indentations are square.

7. The band material of claims 2 or 3, wherein the indentations are triangular.

8. The band material of claims 2 or 3, wherein the indentations are rhomboidal.

9. The band material of claims 2 or 3, wherein the indentations are hexagonal.

10. A seamless orthodontic band having an inside surface, said band being die-worked from metal band material having said inside surface photoetched to define a textured surface for materially enhancing the strength of bonding the band to a tooth with cement.

11. A seamless orthodontic band for attaching an orthodontic appliance to a tooth comprising, a metal die-worked ring-shaped body having a smooth exterior side to which an orthodontic appliance may be attached and a textured internal side for bonding to the tooth, said internal side being textured by being photoetched with a pattern of pockets and die-worked such as to distort the pattern and cause at least some of the pockets to have undercuts, thereby materially enhancing the bonding strength between the band and the tooth.

12. The band of claim 11, wherein the pattern includes a multiplicity of pockets.

13. The band of claim 11, wherein the pattern includes a multiplicity of protuberances.

14. The band of claim 11, wherein the pattern includes a multiplicity of raised dots.

15. The band of claim 11, wherein the pattern includes a multiplicity of doughnut-shaped recesses.

16. A metal blank of thin stainless steel for forming a ring-shaped orthodontic band from a series of dies, said blank being circularly shaped and having a thickness of about 0.006 inch, the outer side of the blank being smooth and the inner side being textured, said textured side being photoetched with a plurality of pockets in aligned rows.

17. The ring blank of claim 16 wherein the pockets are sized in inches of about 0.0035 by 0.0035 with a depth of about 0.001 and a spacing of about 0.005.

18. A metal ring blank of thin stainless steel for forming a ring-shaped orthodontic band from a series of dies, said blank being circularly shaped and having a thickness of about 0.006 inch, the outer side of the blank being smooth and the inner side being textured, said textured side being photoetched with a plurality of doughnut-shaped recesses in aligned rows.

19. A metal blank of thin stainless steel for forming a ring-shaped orthodontic band from a series of dies, said blank being circularly shaped and having a thickness of about 0.006 inch, the outer side of the blank being smooth and the inner side being textured, said textured side being photoetched with a plurality of pockets in staggered rows.

20. The ring blank of claim 19, wherein the pockets are sized in inches of about 0.0085 by 0.0085 with a depth of about 0.001 and a spacing of about 0.005.

21. A metal ring blank of thin stainless steel for forming a ring-shaped orthodontic band from a series of dies, said blank being circularly shaped and having a thickness of about 0.006 inch, the outer side of the blank being smooth and the inner side being textured, said textured side being photoetched with a plurality of doughnut-shaped recesses in staggered rows.

22. Metal band material for making tubular orthodontic bands to be attached to a tooth with a dental cement, said material being in flat sheet or strip form and being photoetched on one side which becomes the inside surface of the band, and said photoetched side including a plurality of rows of spaced apart pockets, Whereby said pockets coact with the cement when attaching the band to a tooth to materially enhance the strength of the cement bond between the band and the tooth, said pockets in inches being about 0.0085 by 0.0085 with a depth of about 0.001 and a spacing between pockets of about 0.005.

23. The band material of claim 22, wherein the pockets in adjacent rows are aligned.

24. The band material of claim 22, wherein the pockets in adjacent rows are staggered.

25. A metal blank of thin stainless steel for forming a ring-shaped orthodontic band from a series of dies, said blank being sized and shaped to be die-workable into a band and having a thickness of about from 0.005 to 0.007 inch, the outer side of the blank being smooth and the inner side being textured, said textured side being photoetched with a plurality of rows of pockets.

26. The metal blank of claim 25, wherein the pockets in adjacent rows are aligned.

27. The metal blank of claim 25, wherein the pockets in adjacent rows are staggered.

* * * * *

UNITED STATES PATENT AND TRADEMARK OFFICE
CERTIFICATE OF CORRECTION

PATENT NO. : 5,441,409
DATED : August 15, 1995
INVENTOR(S) : Lee H. Tuneberg

It is certified that error appears in the above-identified patent and that said Letters Patent is hereby corrected as shown below:

Col. 10, line 8, change "Whereby" to --whereby--.

Signed and Sealed this

Second Day of January, 1996

Attest:

BRUCE LEHMAN

Attesting Officer

Commissioner of Patents and Trademarks